(12) United States Patent
Yang et al.

(10) Patent No.: US 9,057,427 B2
(45) Date of Patent: *Jun. 16, 2015

(54) DEVICE FOR CONTROLLING MOTION OF ANTI-COLLISION SWITCH AND MEDICAL DIAGNOSIS APPARATUS EMPLOYING THE SAME

(71) Applicant: SAMSUNG ELECTRONICS CO., LTD., Suwon-si, Gyeonggi-do (KR)

(72) Inventors: Chang-jin Yang, Seoul (KR); Jung-min Kim, Yeongdeok-gun (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/161,059

(22) Filed: Jan. 22, 2014

(65) Prior Publication Data

US 2014/0130256 A1 May 15, 2014

Related U.S. Application Data

(63) Continuation of application No. 13/951,914, filed on Jul. 26, 2013, now Pat. No. 8,661,584.

(30) Foreign Application Priority Data

Sep. 6, 2012 (KR) ........................ 10-2012-0098963

(51) Int. Cl.
*A61B 6/04* (2006.01)
*F16H 21/44* (2006.01)
(Continued)

(52) U.S. Cl.
CPC ........... *F16H 21/44* (2013.01); *Y10T 74/18912* (2015.01); *Y10T 74/18896* (2015.01);
(Continued)

(58) Field of Classification Search
CPC ....... A61G 7/015; A61G 7/018; A61G 7/002; A61G 7/012; A61G 13/02; A61G 13/06; A61G 13/08; A61B 6/04; A61B 6/0407; A47B 21/03; A47B 23/00
USPC ....... 5/601, 600, 943, 613, 616, 81.1 R, 86.1; 378/208, 209, 204, 205, 20; 108/102
See application file for complete search history.

(56) References Cited

U.S. PATENT DOCUMENTS

| 3,822,875 A | 7/1974 | Schmedemann |
|---|---|---|
| 5,156,166 A | 10/1992 | Sebring |

(Continued)

FOREIGN PATENT DOCUMENTS

| CN | 201327994 | 10/2009 |
|---|---|---|
| CN | 102058415 | 5/2011 |

(Continued)

OTHER PUBLICATIONS

Extended European Search Report issued Nov. 26, 2013 in corresponding European Application No. 13175830.2.
(Continued)

*Primary Examiner* — Robert G Santos
(74) *Attorney, Agent, or Firm* — Staas & Halsey LLP (57) ABSTRACT

In a device for controlling an operation of an anti-collision switch, the anti-collision switch is provided in a support close to a guide frame that is provided at at least one of both lateral sides of a table frame, to prevent collision of the table frame that is supported on the table support to be capable of moving in a lengthwise direction. The device includes a first lever coupled to the table support so that at least a portion of the first lever moves in a vertical direction according to deformation of the guide frame, and a second lever pressing the anti-collision switch in a normal state and, when a vertical movement of the first lever deviates from a preset height, being moved up by the first lever to remove pressing of the anti-collision switch and operate the anti-collision switch.

17 Claims, 4 Drawing Sheets

(51) Int. Cl.
    *A61G 7/018*      (2006.01)
    *A61B 6/10*      (2006.01)
    *H01H 3/04*      (2006.01)

(52) U.S. Cl.
CPC .............. *A61G7/018* (2013.01); *A61B 6/0457* (2013.01); *A61B 6/105* (2013.01); *A61G 2203/726* (2013.01); *A61B 6/0407* (2013.01); *H01H 3/04* (2013.01)

(56) References Cited

U.S. PATENT DOCUMENTS

| | | | |
|---|---|---|---|
| 8,006,625 | B2 | 8/2011 | Yang |
| 8,191,190 | B2 | 6/2012 | Zapata |
| 8,661,584 | B1 * | 3/2014 | Yang et al. ................ 5/601 |
| 2009/0101040 | A1 | 4/2009 | Yang |
| 2010/0287703 | A1 | 11/2010 | Zapata |
| 2014/0059767 | A1 * | 3/2014 | Yang et al. ................ 5/601 |
| 2014/0130256 | A1 * | 5/2014 | Yang et al. ................ 5/601 |

FOREIGN PATENT DOCUMENTS

| | | |
|---|---|---|
| FR | 2 685 058 | 12/1991 |
| FR | 2 770 396 | 11/1997 |
| JP | 6-14918 | 1/1994 |
| JP | 2002-219118 | 8/2002 |
| JP | 2006-55518 | 3/2006 |
| KR | 10-2004-0020794 | 3/2004 |

OTHER PUBLICATIONS

Korean Notice of Allowance issued Oct. 30, 2013 in corresponding Korean Application No. 10-2012-0098963.
U.S. Notice of Allowance issued Oct. 16, 2013 in copending U.S. Appl. No. 13/951,914.
U.S. Appl. No. 13/951,914, filed Jul. 26, 2013, Chang-jin Yang, Samsung Electronics Co., Ltd.
Chinese Office Action issued Mar. 2, 2015 in corresponding Chinese Patent Application No. 201310403933.0.

* cited by examiner

DEVICE FOR CONTROLLING MOTION OF ANTI-COLLISION SWITCH AND MEDICAL DIAGNOSIS APPARATUS EMPLOYING THE SAME

CROSS-REFERENCE TO RELATED APPLICATIONS

This application is a continuation of U.S. application Ser. No. 13/951,914, filed Jul. 26, 2013, which claims the benefit of Korean Patent Application No. 10-2012-0098963, filed on Sep. 6, 2012, in the Korean Intellectual Property Office, the disclosure of which is incorporated herein in its entirety by reference.

BACKGROUND

1. Field

One or more embodiments relate to a device for controlling the operation of an anti-collision switch capable of controlling an operation motion, and a table for a medical diagnosis apparatus employing the device.

2. Description of the Related Art

A medical diagnosis apparatus, such as an X-ray photographing apparatus, has a table guide structure capable of sliding a table to a position where an examination operation, such as an X-ray irradiation, is performed. In other words, in the table guide structure of an X-ray photographing apparatus, an examinee (a patient) is laid on the table at a comfortable position, and the table slides to a position where X-ray photographing is easily performed. Thus, the X-ray photographing, which is a medical examination operation, may be easily performed.

The table guide structure is equipped with a lift for elevating the table for convenience of an examinee. Also, an anti-collision switch is provided on the table to prevent a wheel chair or an examinee from being pressed and damaged or hurt by the table that is lowered. To avoid malfunction of the table due to deformation of a table frame, the anti-collision switch has a structure to maintain a gap from the table frame to cover the predictable maximum deformation amount or a structure that is specially manufactured to be capable of controlling a motion of the table to cover the deformation.

SUMMARY

Additional aspects and/or advantages of one or more embodiments will be set forth in part in the description which follows and, in part, will be apparent from the description, or may be learned by practice of one or more embodiments of disclosure. One or more embodiments are inclusive of such additional aspects.

One or more embodiments provide a device for controlling the operation of an anti-collision switch which may prevent a vertical movement of a table frame or generation of a collision sound due to the vertical movement by forming a gap between the anti-collision switch and the table frame and may reduce much cost needed for separately manufacturing a switch capable of controlling a motion, and a table for a medical diagnosis apparatus employing the device.

According to an aspect of one or more embodiments, a device for controlling an operation of an anti-collision switch, the anti-collision switch being provided in a table support adjacent to a guide frame that is provided at at least one of both lateral sides of a table frame that is supported on the table support to be capable of moving in a lengthwise direction, may include a first lever coupled to the table support so that at least a portion of the first lever may move in a vertical direction according to deformation of the guide frame, and a second lever pressing the anti-collision switch in a normal state and, when a vertical movement of the first lever deviates from a preset height, being moved up by the first lever to release the anti-collision switch.

A gap adjustment member for adjusting a gap between the first lever and the second lever may be provided on the first lever such that the gap adjustment member collides against the second lever when the first lever is moved upwardly. The gap adjustment member may be any one of a bolt, a screw, and a protruding pin. Since the gap with the second lever may be adjusted by the gap adjustment member, an operating motion to operate the anti-collision switch may be adjusted. Furthermore, since a bolt, a screw, or a protruding pin may be employed as the gap adjustment member, the operating motion may be adjusted.

The device may further include a first elastic member elastically pressing the first lever toward the guide frame, and a second elastic member elastically pressing an end of the second lever toward the anti-collision switch. One end of the first elastic member may be fixed on the first lever and the other end of the first elastic member may be fixed on the table support. One end of the second elastic member may be fixed on the second lever and the other end of the second elastic member may be fixed on the first lever. One end of the second elastic member may be fixed on the second lever and the other end of the second elastic member may be fixed on the table support. Since the first elastic member may cause the first lever to remain in contact with the guide frame, a movement of the table frame or generation of a collision sound due to the movement of the table frame may be reduced.

The device may further include a bearing that is rotatably coupled to the first lever and directly contacts the guide frame. The bearing may reduce a friction generated when the guide frame slides over the first lever.

The first lever may be pivotably coupled to the table support. The first lever may include a first portion where a rotational axis that is pivotably coupled to the table support is disposed and a second portion extending from the first portion in a direction parallel to the guide frame. The device may further include a first elastic member that has one end fixed on the second portion of the first lever and the other end fixed on the table support and elastically presses the second portion of the first lever toward the guide frame.

The first lever may include a third portion that extends from the first portion in the same direction in which the second portion extends and is disposed above at least a portion of the second lever. The device may further include a second elastic member that has one end fixed on the second lever and the other end fixed on the third portion of the first lever so that one side of the second lever elastically presses the second lever in a direction to press the anti-collision switch.

The second lever may include a first portion where a rotational axis that is pivotably coupled to the first lever is disposed, a second portion formed by being bent from the first portion so that an end of the second elastic member is fixed on the second portion, and a third portion formed by being bent from the first portion to press the anti-collision switch from above. A gap adjustment member for adjusting a gap between the first lever and the second portion of the second lever may be provided on the first portion of the first lever facing the second portion of the second lever.

The anti-collision switch may be a press button switch or a touch sensor. The first lever may be coupled to the table support to be capable of linearly moving in a vertical direction. The second lever may be coupled to the table support to be capable of pivoting or linearly moving in a vertical direction.

According to another aspect of the present invention, a table for a medical diagnosis apparatus may include a table support, a table frame supported on the table support to be capable of moving in a lengthwise direction, a guide frame provided at at least one of both lateral sides of the table frame, an anti-collision switch provided in the table support close to the guide frame and operating when a collision occurs in the table frame, a device for controlling an operation of the anti-collision switch, and a control unit that stops a movement of the table frame when the anti-collision switch is operated. In the table for a medical diagnosis apparatus, the device for controlling an operation of the anti-collision switch may include a first lever coupled to the table support so that at least a portion of the first lever moves in a vertical direction according to deformation of the guide frame, and a second lever pressing the anti-collision switch in a normal state and, when a vertical movement of the first lever deviates from a preset height, being moved up by the first lever to release the anti-collision switch.

The height of the table support may be adjustable. For example, the table support may have a two-step structure of a lower support and an upper support capable of moving up and down.

The table may be a table for an X-ray photographing apparatus.

BRIEF DESCRIPTION OF THE DRAWINGS

These and/or other aspects will become apparent and more readily appreciated from the following description of embodiments, taken in conjunction with the accompanying drawings of which.

DETAILED DESCRIPTION

Reference will now be made in detail to one or more embodiments, illustrated in the accompanying drawings, wherein like reference numerals refer to like elements throughout. In this regard, embodiments of the present invention may be embodied in many different forms and should not be construed as being limited to embodiments set forth herein, as various changes, modifications, and equivalents of the systems, apparatuses and/or methods described herein will be understood to be included in the invention by those of ordinary skill in the art after embodiments discussed herein are understood. Accordingly, embodiments are merely described below, by referring to the figures, to explain aspects of the present invention.

As used herein, the term "and/or" includes any and all combinations of one or more of the associated listed items. Expressions such as "at least one of," when preceding a list of elements, modify the entire list of elements and do not modify the individual elements of the list.

Figure 1:
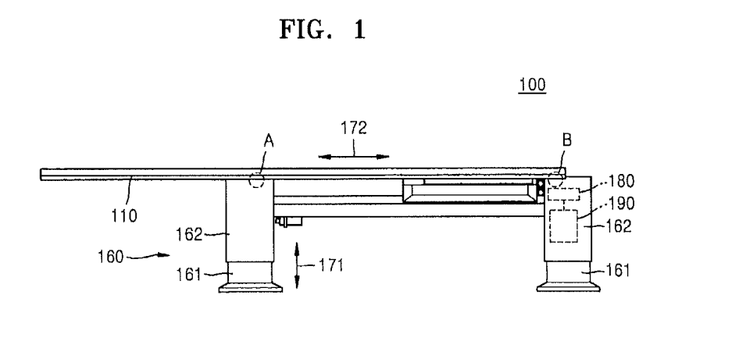
FIG. 1 is a side view schematically illustrating a table for a medical diagnosis apparatus according to one or more embodiments.
Figure 2:
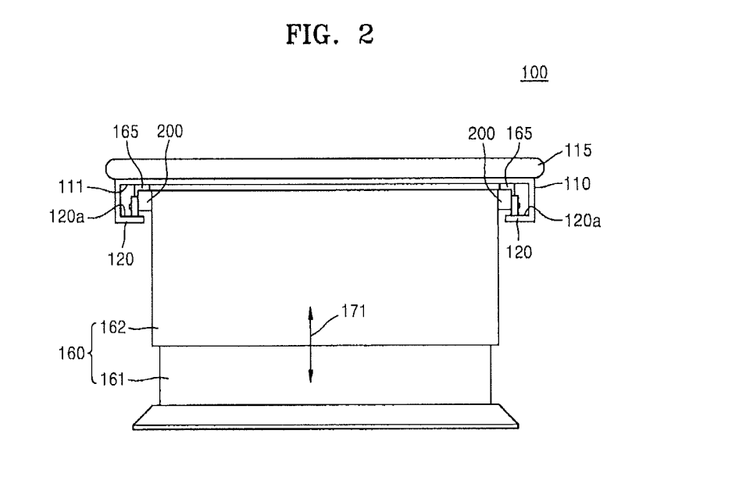
FIG. 2 is a front side view schematically illustrating a table according to one or more embodiments, such as the table of FIG. 1.

FIG. 1 is a side view schematically illustrating a table 100 for a medical diagnosis apparatus according to one or more embodiments. FIG. 2 is a front side view schematically illustrating a table according to one or more embodiments, such as the table 100 of FIG. 1.

Referring to FIGS. 1 and 2, the table 100 for a medical diagnosis apparatus may include a table frame 110 and a table support 160 for supporting the table frame 110. The table frame 110 may be used for an examinee (a patient) receiving a diagnosis to lie thereon. For example, the table frame 110 may have a rectangular upper surface. When the table 100 for a medical diagnosis apparatus is used as a table of an X-ray photographing apparatus, the table frame 110 may be formed of a material, such as plastic, through which X-rays may pass. An X-ray source (not shown) may be positioned above the table frame 110. An X-ray detection apparatus (not shown) for detecting the X-rays passing through the table frame 110 may be positioned under the table frame 110. Thus, X-ray photographing may be performed when an examinee is lying on the table frame 110.

The table support 160 may have, for example, a 2-step structure of a lower support 161 and an upper support 162 capable of moving in a vertical direction 171, that is, ascending and descending, with respect to the lower support 161. A variety of structures capable of adjusting height may be employed as the table support 160. Also, an ascending/descending actuating unit 180 may be provided inside or outside the table support 160 to automatically control the ascending/descending of the table frame 110 by a user operation. A well-known device such as a hydraulic pump or a motor may be employed as the ascending/descending actuating unit 180.

The table frame 110 may be supported to be slidable in a lengthwise direction 172 with respect to the table support 160. As an example of a sliding support structure capable of moving in the lengthwise direction 172, a plurality of load support wheels 165 of FIG. 2 may be provided in areas A and B at both lateral sides of the table support 160. As the load support wheels 165 support a lower portion 111 at both lateral sides of the table frame 110 to be capable of sliding, the table frame 110 may move in the lengthwise direction 172 with respect to the table support 160. Also, a sliding actuating unit (not shown), such as a motor, may be provided in the table support 160 and thus the table frame 110 may be controlled to automatically move in the lengthwise direction 172 by a user operation. Furthermore, a moving structure (not shown) to move the table frame 110 in a widthwise direction of the table frame 110 may be further provided in the table support 160.

A guide frame 120 may be provided at at least one of both lateral sides of the table frame 110. The guide frame 120 may have a bent shape so that a predetermined space may be provided therein. The guide frame 120 may be formed integrally with the table frame 110 or separately therefrom and attached to the table frame 110. As the table frame 110 moves in the lengthwise direction 172, the guide frame 120 integrally formed with the table frame 110 also may move in the lengthwise direction 172. The load support wheels 165 located in the predetermined space 121 provided by the guide frame 120 may be protected and visually covered by the guide frame 120.

Figure 3:
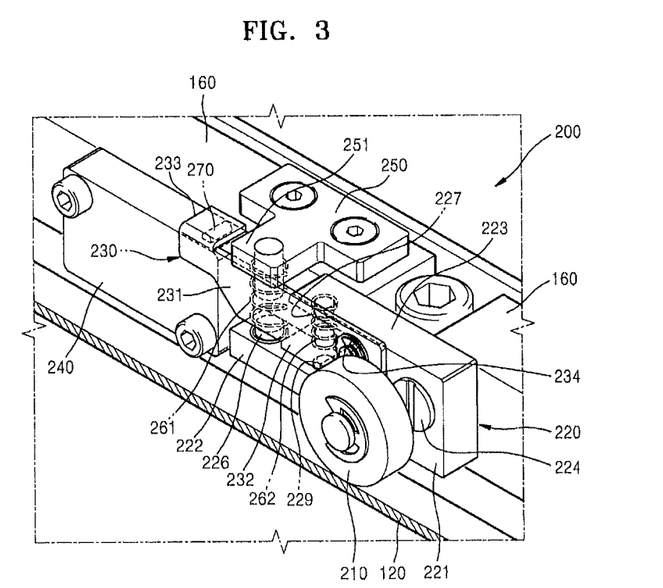
FIG. 3 is a perspective view schematically illustrating a device for controlling the operation of an anti-collision switch employed in a table according to one or more embodiments, such as the table of FIG. 1.

A control unit 190 for controlling the ascending/descending motion of the table support 160 and the sliding motion of the table frame 110 may be provided inside or outside the table support 160. When collisions occur as the table frame 110 moves, as described below, an anti-collision switch 270 as shown in FIG. 3 may be operated. Thus, information about the collision may be provided to the control unit 190, and the control unit 190 may stop the ascending/descending motion of the table support 160 or the sliding motion of the table frame 110.

A switch operation control device 200 may be fixed at any one lateral side or both lateral sides of the table support 160. One or more switch operation control devices 200 may be provided on each lateral side of the table support 160. For example, the switch operation control device 200 may be provided in at least one of the areas A and B. The switch operation control device 200 may be located in the predetermined space formed by the bent shape of the guide frame 120 so that the switch operation control device 200 may be protected and visually covered by the guide frame 120.

Figure 4:
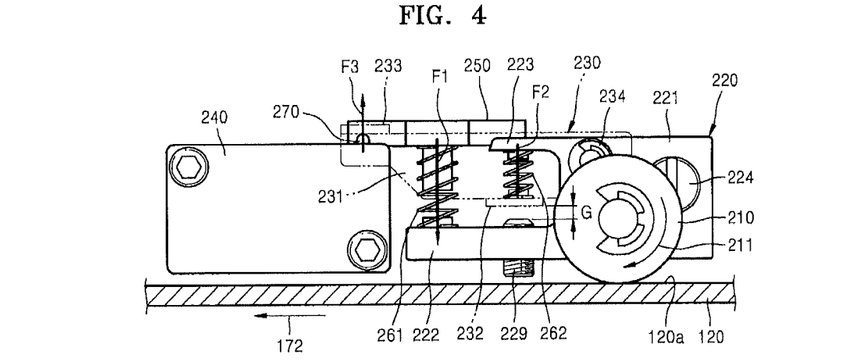
FIG. 4 is a cross-sectional view schematically illustrating the device for controlling the operation of an anti-collision switch according to one or more embodiments, such as the anti-collision switch of FIG. 3, showing a relationship between forces applied to each constituent elements.

FIG. 3 is a perspective view illustrating a switch operation control device according to one or more embodiments in detail. FIG. 4 is a front side view of switch operation control device according to one or more embodiments. In FIGS. 3 and 4, a second lever 230 is indicated by a hidden line to clearly show the internal structure of the switch operation control device 200.

Referring to FIGS. 3 and 4, the switch operation control device 200 may include a first lever 220 that moves in a vertical direction according to deformation of the guide frame 120 and a second lever 230 operated by the first lever 220 when the deformation of the guide frame 120 deviates from a predetermined gap. The anti-collision switch 270 may be provided to possibly prevent an examinee or a wheelchair from being pressed and hurt or damaged by the table frame 110 that descends.

The first lever 220 may be coupled to the table support 160 to be capable of pivoting around a rotational axis 224 so that at least a part, that is, a second portion 222, of the first lever 220 may move vertically with respect to the table support 160.

A bearing 210 may be provided at the first lever 220 to reduce friction between the first lever 220 and the guide frame 120. In other words, the bearing 210 is pivotably coupled to the first lever 220 and contacts an inner surface 120a of the guide frame 120. As the table frame 110 moves in the lengthwise direction 172, the guide frame 120 integrally formed with the table frame 110 also moves in the lengthwise direction 172 and thus the bearing 210 contacting an inner surface 120a of the guide frame 120 rotates in a direction 211. A rotational axis of the bearing 210 may be separated a predetermined distance from the rotational axis 224 of the first lever 220 in a lengthwise direction 172 of the guide frame 120. When the guide frame 120 is deformed to be curved vertically, as described below, the bearing 210 may move in an upward direction 212 of FIG. 5A as the guide frame 120 moves in the lengthwise direction 172. Accordingly, the first lever 220 may pivot around the rotational axis 224. The bearing 210 may be omitted, though friction may be generated. When the bearing 210 is omitted, one side of the first lever 220 may directly contact the guide frame 120.

The first lever 220 may include a first portion 221 pivotably coupled to the table support 160, and the second portion 222 and a third portion 223 extending from the first portion 221 in one direction parallel to the guide frame 120. The second portion 222 of the first lever 220 may be located closer to a lower side, that is, the guide frame 120, compared to the third portion 223. The second portion 222 may be longer than the third portion 223. The second portion 222 and the third portion 223 of the first lever 220 may be located, together with the bearing 210, at the same side with respect to the rotational axis 224 of the first lever 220. Thus, when the bearing 210 moves in the vertical direction 212 of FIG. 5A, the first lever 220 may pivot around the rotational axis 224. Accordingly, the second portion 222 and the third portion 223 of the first lever 220 may move in the vertical direction 212.

A gap adjustment member 229 may be provided at the second portion 222 of the first lever 220. The gap adjustment member 229 may be located where the first lever 220 may contact one side of the second lever 230 when the first lever 220 pivots. The gap adjustment member 229 is a protruding member having an end portion 229a whose height may be adjustable, for example, a bolt, a screw, or a protruding pin. When a bolt or a screw is employed as the gap adjustment member 229, a gap G between the end portion 229a of the gap adjustment member 229 and a second portion 232 of the second lever 230 may be easily adjusted by turning the bolt or screw. The gap G between the end portion 229a of the gap adjustment member 229 and the second portion 232 of the second lever 230 may be provided to prevent unintended malfunction due to undesirable deformation of the table frame 110.

The second lever 230 may include a first portion 231 that may be pivotably coupled to the first lever 220 via a rotational axis 234.

The second lever 230 may further include a second portion 232 that may be formed by bending a part of a lower end of the first portion 231 of the second lever 230. The second portion 232 of the second lever 230 may be separated by a predetermined gap from a lower surface of the third portion 223 of the first lever 220 and may face the lower surface of the third portion 223. The second portion 232 of the second lever 230 may be inserted in a space between the second portion 222 and the third portion 223 of the first lever 220. The gap adjustment member 229 mat be located at a predetermined position of the second portion 222 of the first lever 220 and may face the second portion 232 of the second lever 230.

Also, the second lever 230 may include a third portion 233 that may be formed by bending an end portion of the first portion 231 of the second lever 230 to be able to press the anti-collision switch 270 located at an upper portion of a first fixed block 240. The first fixed block 240 may be separated by a predetermined distance from an end portion of the second portion 222 of the first lever 220 and may be fixed at one side of the table support 160. The first fixed block 240 may be integrally formed with the table support 160.

The anti-collision switch 270 may be located under the third portion 233 of the second lever 230. The anti-collision switch 270 may be installed on an upper portion of the first fixed block 240 or on the table support 160. A push button switch may be employed as the anti-collision switch 270. The push button switch is a switch that is operated when a button is pressed and in which the button is returned to the original state when the button is released. The push button switch is well known in the field to which the present invention pertains. The anti-collision switch 270 of the first fixed block 240 may be located under the third portion 233 of the second lever 230 and may be in a state of being pressed by the third portion 233 of the second lever 230 in a normal state. Alternatively, a touch sensor for sensing contact may be employed as the anti-collision switch 270. As described below, when the table frame 110 meets against an obstacle, the anti-collision switch 270 may be operated to stop the movement of the table frame 110.

A second fixed block 250 may include a protruding portion 251 that may be separated from the second portion 222 of the first lever 220 to face the same, and may be fixed on the table support 160. The protruding portion 251 of the second fixed block 250 may be located outside pivot ranges of the first lever 220 and the second lever 230. A first elastic member 261 may be provided between the second portion 222 of the first lever 220 and the protruding portion 251 of the second fixed block 250, which face each other. One end of the first elastic member 261 may be fixed on an upper surface of the second portion 222 of the first lever 220 and the other end of the first elastic member 261 may be fixed on a lower surface of the protruding portion 251 of the second fixed block 250. The first elastic member 261 may be fixed, for example, by using a protrusion or a concavity formed at the upper surface of the second portion 222 of the first lever 220 and the lower surface of the protruding portion 251 of the second fixed block 250. The first elastic member 261 may be, for example, a spring or rubber. The first elastic member 261 may elastically press the second portion 222 of the first lever 220 toward the guide frame 120. In other words, an operating force F1 of the first elastic member 261 may act in a direction in which the protruding portion 251 of the second fixed block 250 pushes the second portion 222 of the first lever 220. The bearing 210 may be maintained in a state of contacting the guide frame 120 by the operating force F1 of the first elastic member 261. Thus, a vertical movement of the table frame 110 may be restricted and generation of sound from a collision due to the vertical movement may be reduced.

A second elastic member 262 may be located between the third portion 223 of the first lever 220 and the second portion 232 of the second lever 230. One end of the second elastic member 262 may be fixed on the upper surface of the second portion 232 of the second lever 230, and the other end of the second elastic member 262 may be fixed on the lower surface of the third portion 223 of the first lever 220. The second elastic member 262 may be fixed, for example, by using a protrusion or a concavity formed on the upper surface of the second portion 232 of the second lever 230 and the lower surface of the third portion 223 of the first lever 220. An operating force F2 of the second elastic member 262 may act in a direction in which the third portion 223 of the first lever 220 pushes the second portion 232 of the second lever 230.

The operating forces F1 and F2 of the first and second elastic members 261 and 263 may finally act as a force of the second lever 230 to press the anti-collision switch 270. As a reaction to the final force, an operating force F3 that presses the anti-collision switch 270 by pushing upwards of the third portion 233 of the second lever 230 may be generated so that the operating forces F1, F2 and F3 are in an equilibrium state.

Next, the operation of the switch operation control device 200 in the table 100 for a medical diagnosis apparatus according to the present embodiment is described below with reference to FIGS. 1, 4, and 5A through 5D. Referring to FIGS. 1 and 4, the table frame 110 may move in the vertical direction 171 and/or the lengthwise direction 172 so that an examinee may lie on the table frame 110. A state in which the table frame 110 moves while the anti-collision switch 270 is pressed is referred to as a normal state. In the normal state, the anti-collision switch 270 located under the third portion 233 of the second lever 230 is pressed by the third portion 233 of the second lever 230. The movement of the table frame 110, for example, in the vertical direction 171 and/or the lengthwise direction 172, is normally performed.

Figure 5A:
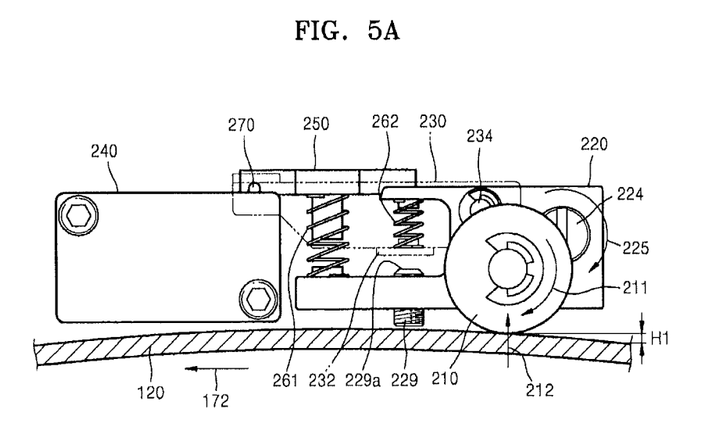
FIGS. 5A through 5D are cross-sectional views schematically illustrating the operation of the device for controlling the operation of an anti-collision switch according to one or more embodiments, such as the anti-collision switch of FIG. 3.
Figure 5B:
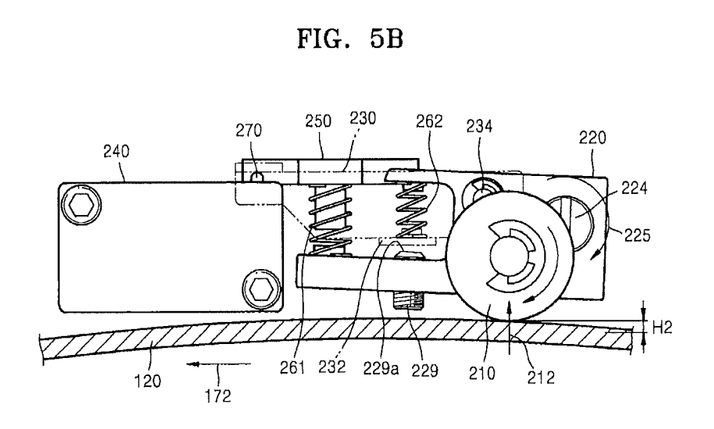
Figure 5C:
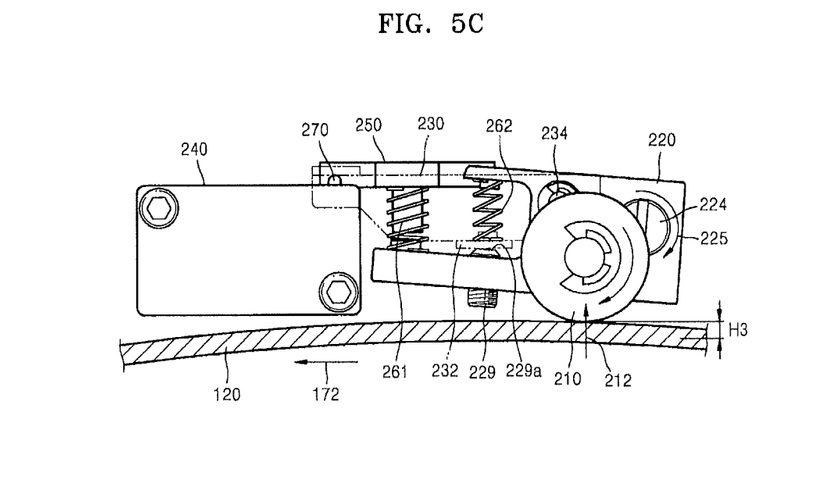

Although the guide frame 120 is assumed to be flat without a deviation in its height, the guide frame 120 may be deformed in the manufacturing or use process. FIGS. 5A through 5C illustrates a case in which the guide frame 120 is curved by height changes H1, H2, and H3. The height changes H1, H2, and H3 are values that sequentially increase.

Referring to FIGS. 5A through 5C, when the table frame 110 of FIG. 1 moves in the lengthwise direction 172, the bearing 210 of the switch operation control device 200 may be rotated along the movement of the guide frame 120. As the guide frame 120 is curved, the bearing 210 may be moved upwardly by the guide frame 120 in the upward direction 212 by the height changes H1, H2, and H3. Since the rotational axis of the bearing 210 and the rotational axis 224 of the first lever 220 may be separated by a predetermined distance from each other in the lengthwise direction 172 of the guide frame 120, the upward movement of the bearing 210 may cause the first lever 220 to slightly rotate in a clockwise direction 225 around the rotational axis 224. Also, since the second lever 230 may be pivotably coupled to the first lever 220, the rotational axis 234 of the second lever 230 may be slightly moved upwardly according to the slight rotation of the first lever 220. In this case, however, the second lever 230 may continue to press the anti-collision switch 270 because the anti-collision switch 270 receives a downward force by the second elastic member 262. In other words, according to the present embodiment, even when a slight deformation is generated in the guide frame 120, the table frame 110 may maintain a normal movement because the anti-collision switch 270 maintains a pressed state.

The above state may be maintained until the end portion 229a of the gap adjustment member 229 contacts the second portion 232 of the second lever 230, as illustrated in FIG. 5C. In other words, even when the bearing 210 and the first lever 220 are gradually moved upwardly as the guide frame 120 is curved, the second lever 230 may continue to press the anti-collision switch 270 because the second portion 232 of the second lever 230 receives the downward force by the second elastic member 262 until the end portion 229a of the gap adjustment member 229 contacts the second portion 232 of the second lever 230. The height change H3 when the end portion 229a of the gap adjustment member 229 contacts the second portion 232 of the second lever 230 may correspond to a limit for the table frame 110 to maintain a normal movement. The limit may be adjusted by the gap G of FIG. 4 between the end portion 229a of the gap adjustment member 229 and the second portion 232 of the second lever 230. In other words, an operation distance to prevent an undesired malfunction due to a deformation defect of the table frame 110, that is, the limit at which the table frame 110 maintains the normal movement, may be set by adjusting the height of the end portion 229a of the gap adjustment member 229. In other words, when the vertical movement of the table frame 110 is performed less than or equal to the height change H3, the gap G between the end portion 229a of the gap adjustment member 229 and the second portion 232 of the second lever 230 may prevent stop of the movement of the table frame 110.

Figure 5D:
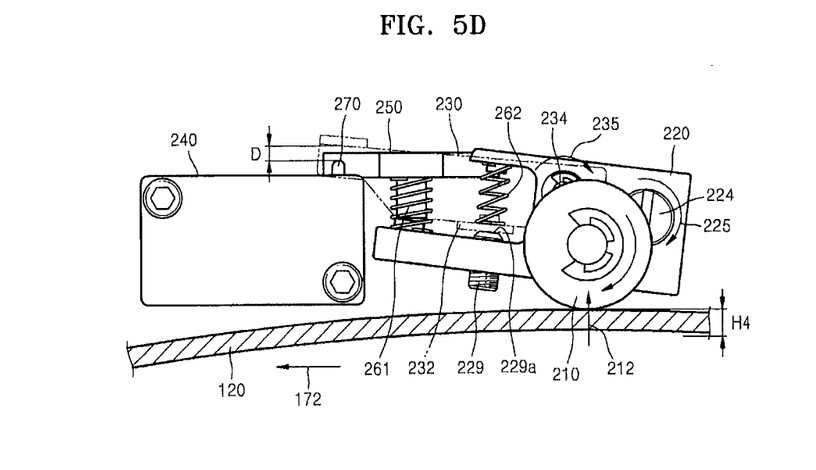

FIG. 5D illustrates that the guide frame 120 is curved by the height change H4. The height change H4 is higher than the set height change H3. When the bearing 210 is moved upwardly by as much as the height change H4, the first lever 220 may rotate and thus the end portion 229a of the gap adjustment member 229 may push upwardly the end portion of the second portion 232 of the second lever 230. Accordingly, in spite of the operating force F2 of the second elastic member 262, the second lever 230 may rotate in a clockwise direction 235 around the rotational axis 234. Accordingly, the third portion 233 of the second lever 230 may be moved upwardly and thus the force pressing the anti-collision switch 270 may be discontinued. Thus, the pressed state of the anti-collision switch 270 may be removed. When the pressed state of the anti-collision switch 270 is removed, a control unit (not shown) of the table 100 for a medical diagnosis apparatus may stop the movement of the table frame 110, for example, the movements in the vertical direction 171 and/or the lengthwise direction 172, thereby possibly preventing an accident according to the movement of the table frame 110.

When the table frame 110 collides against an examinee or an unspecified object, for example, a wheelchair, during elevation, the table frame 110 may be moved upwardly. As such, when the table frame 110 is moved upwardly, the guide frame 120 is moved upwardly and the bearing 210 of the switch operation control device 200 may be simultaneously moved upwardly by the guide frame 120. When the height at which the bearing 210 is pushed in the upward direction 212 is less than the height change H3, the pressing of the anti-collision switch 270 may be maintained by the same operation described with reference to FIGS. 5A and 5B and thus the normal state may be maintained. In this point of view, the gap G between the end portion 229a of the gap adjustment member 229 and the second portion 232 of the second lever 230 may be the operation distance of the anti-collision switch 270 to prevent malfunction due to collision based on a reference value. When an impact received by the table frame 110 is great and thus the height at which the bearing 210 is pushed in the upward direction 212 is greater than the height change H3, the anti-collision switch 270 is released by the same operation described above with respect to FIG. 5D for the safety of an examinee or to prevent damage of a medical diagnosis apparatus. Thus, the movement of the table frame 110 may be stopped. The height change H3 may be directly related to the size of the gap G of FIG. 4. Thus, an operation motion to determine whether the anti-collision switch 270 is to be operated may be adjusted by adjusting the height of the gap adjustment member 229.

In the switch operation control device 200, since a well-known switch, such as a push button switch or a touch sensor switch, may be used as the anti-collision switch 270 without using a switch with a special specification, manufacturing costs may be reduced. Also, since a magnitude of a motion within which an operation of the movement of table frame 110 is allowed may be freely adjusted by the gap adjustment member 229, the switch operation control device 200 may be easily applied to a variety of specifications of the table 100 for a medical diagnosis apparatus Although in the above-described embodiment the first lever 220 may be pivotably coupled to the table support 160, the present invention is not limited thereto. The pivotable coupling of the first lever 220 is one of the coupling examples in which at least one end of the first lever 220, that is, a portion where the gap adjustment member 229 is located, is movable upwardly. In another example, a vertically linear groove may be formed in the table support 160 and a protruding portion to be inserted in the groove of the table support 160 may be formed on the first lever 220. Accordingly, the first lever 220 may be coupled to the table support 160 to be capable of moving linearly in the vertical direction as a whole. In this case, as the bearing 210 is moved upwardly, the first lever 220 may be moved upwardly as a whole. A dynamic relationship among the first lever, 220, the second lever 230, and the first and second elastic members 261 and 262 in the above case may be substantially the same as that in the case of pivotably coupling the first lever 220 to the table support 160.

Likewise, although in the above-described embodiment the second lever 230 may be pivotably coupled to the first lever 220, the present invention is not limited thereto. The pivotably coupling of the second lever 230 is one of the coupling examples in which at least one end of the second lever 230, that is, a portion where the third portion 233 is located, may be movable upwardly. In another example, a vertically linear groove may be formed in the table support 160 and a protruding portion to be inserted in the groove of the table support 160 may be formed on the second lever 230. Accordingly, the second lever 230 may be coupled to the table support 160 to be capable of moving linearly in the vertical direction as a whole. In this case, the second lever 230 may remain the same without a change in its position or be moved upwardly according to a degree of upward movement of the first lever 220. When the second lever 230 is moved upwardly, the pressed state of the anti-collision switch 270 may be removed. A dynamic relationship among the first lever, 220, the second lever 230, and the first and second elastic members 261 and 262 in the above case may be substantially the same as that in the case of pivotably coupling the second lever 230 to the first lever 220. In another case, the second lever 230 may be coupled to the first lever 220 to be capable of moving linearly in the vertical direction. A dynamic relationship among the first lever 220, the second lever 230, and the second elastic member 262 may be substantially the same as that in the case of pivotably coupling the second lever 230 to the first lever 220.

Although in the above-described embodiment one end of the second elastic member 262 may be fixed on the first lever 220, the present invention is not limited thereto. Since the second elastic member 262 may perform a function to press the second lever 230 toward the anti-collision switch 270 by the operating force F2, the second elastic member 262 may be variously deformed within a range of keeping the function. For example, one end of the second elastic member 262 may be fixed on the second fixed block 250 or may be directly fixed on the table support 160. In this case, the third portion 223 of the first lever 220 that fixes one end of the second elastic member 262 may be omitted because the third portion 223 may not be necessary. In any case, the second elastic member 262 may apply the operating force F2 as depicted in FIG. 4 by which the second elastic member 262 may downwardly press the second portion 232 of the second lever 230.

Although in the present embodiment the first and second fixed blocks 240 and 250 are provided separated from the table support 160 and fixedly coupled to the table support 160, the present invention is not limited thereto. The first and second fixed blocks 240 and 250 may be integrally formed with the table support 160.

As described above, a device for controlling the operation of an anti-collision switch according to the present invention may prevent a movement of a frame and generation of a collision sound due to the movement of the frame so that the quality of a product may be improved and an operating motion of the anti-collision switch may be adjusted according to specifications. Thus, the device may be applied to a variety of specifications of a table for a medical diagnosis apparatus.

In one or more embodiments, the term apparatus should be considered synonymous with elements of a physical system, not limited to a single device or enclosure or all described elements embodied in single respective enclosures in all embodiments, but rather, depending on embodiment, is open to being embodied together or separately in differing enclosures and/or locations through differing hardware elements.

While aspects of the present invention has been particularly shown and described with reference to differing embodiments thereof, it should be understood that these embodiments should be considered in a descriptive sense only and not for purposes of limitation. Descriptions of features or aspects within each embodiment should typically be considered as available for other similar features or aspects in the remaining embodiments. Suitable results may equally be achieved if the described techniques are performed in a different order and/or if components in a described system, architecture, device, or circuit are combined in a different manner and/or replaced or supplemented by other components or their equivalents.

Thus, although a few embodiments have been shown and described, with additional embodiments being equally available, it would be appreciated by those skilled in the art that changes may be made in these embodiments without departing from the principles and spirit of the invention, the scope of which is defined in the claims and their equivalents.

What is claimed is:

1. A device for controlling an operation of an anti-collision switch, the device comprising:
    a first lever coupled to a support adjacent to a guide frame and pressing the anti-collision switch in a normal state such that when a vertical movement of the first lever according to deformation of the guide frame deviates from a preset height the first lever releases the anti-collision switch; and
    a first elastic member elastically pressing an end of the first lever toward the anti-collision switch.

2. The device of claim 1, further comprising:
    a second lever coupled to the support so that at least a portion of the second lever moves in a vertical direction according to the deformation of the guide frame such that when a vertical movement of the second lever deviates from a preset height the first lever is moved up by the second lever to release the anti-collision switch; and
    a second elastic member elastically pressing the second lever toward the guide frame.

3. The device of claim 2, wherein the second lever comprises:
    a first portion where a rotational axis that is pivotably coupled to the support is disposed;
    a second portion extending from the first portion in a direction parallel to the guide frame; and
    a third portion that extends from the first portion in the same direction in which the second portion extends and is disposed above at least a portion of the first lever.

4. The device of claim 3, wherein the first lever comprises:
    a first portion where a rotational axis that is pivotably coupled to the second lever is disposed;
    a second portion formed by being bent from the first portion so that an end of the first elastic member is fixed on the second portion; and
    a third portion formed by being bent from the first portion to press the anti-collision switch from above.

5. The device of claim 4, wherein a gap adjustment member for adjusting a gap between the second lever and the first lever is provided on the second lever such that the gap adjustment member collides against the first lever when the second lever is moved upwardly.

6. The device of claim 5, wherein the anti-collision switch is provided in a table support adjacent to the guide frame that is provided at at least one of both lateral sides of a table frame that is supported on the table support to be capable of moving in a lengthwise direction.

7. The device of claim 5, wherein the gap adjustment member is any one of a bolt, a screw, and a protruding pin.

8. The device of claim 2, wherein one end of the second elastic member is fixed on the second lever and the other end of the second elastic member is fixed on the support.

9. The device of claim 2, wherein one end of the first elastic member is fixed on the first lever and the other end of the first elastic member is fixed on the second lever.

10. The device of claim 2, wherein one end of the first elastic member is fixed on the first lever and the other end of the first elastic member is fixed on the support.

11. The device of claim 2, wherein the second lever is pivotably coupled to the support.

12. The device of claim 2, wherein the second lever is coupled to the support to be capable of linearly moving in a vertical direction.

13. The device of claim 2, wherein the support is a table support of a table for a medical diagnosis apparatus and the table further comprises:
    a table frame supported on the table support to be capable of moving in a lengthwise direction;
    a guide frame provided at at least one of both lateral sides of the table frame.

14. The device of claim 13, wherein the height of the table support is adjustable.

15. The device of claim 13, wherein the table is a table for an X-ray photographing apparatus.

16. The device of claim 1, wherein the anti-collision switch is a press button switch or a touch sensor.

17. The device of claim 1, wherein the first lever is coupled to the support to be capable of pivoting or linearly moving in a vertical direction.

* * * * *